United States Patent [19]

Suzuki et al.

[11] 3,988,333
[45] Oct. 26, 1976

[54] TRI-SUBSTITUTED ALUMINUM SALTS OR DI-SUBSTITUTED ALUMINUM SALTS OF CARBOXYL GROUP-CONTAINING, PHARMACEUTICALLY EFFECTIVE COMPOUNDS

[75] Inventors: Yasushi Suzuki, Yokohama; Toshihisa Itaya, Kawasaki, both of Japan

[73] Assignee: Teikoku Hormone Mfg. Co., Ltd., Tokyo, Japan

[22] Filed: Nov. 26, 1974

[21] Appl. No.: 527,415

Related U.S. Application Data

[63] Continuation of Ser. No. 236,347, March 20, 1972, Pat. No. 3,865,857.

[52] U.S. Cl. .................. 260/448 R; 260/239.1; 260/270 R; 260/295 R; 260/299; 260/343.7; 260/346.1 M; 260/397.1; 260/414; 260/999
[51] Int. Cl.² .................................. C07F 5/06
[58] Field of Search .................... 260/448 R, 448 B

[56] References Cited
UNITED STATES PATENTS

| | | | |
|---|---|---|---|
| 3,173,934 | 3/1965 | Davison | 260/448 B X |
| 3,184,490 | 5/1965 | Davison | 260/448 R X |
| 3,409,655 | 11/1968 | Seki et al. | 260/448 R |
| 3,492,329 | 1/1970 | Davison et al. | 260/448 B |
| 3,865,857 | 2/1975 | Suzuki et al. | 260/448 R |

FOREIGN PATENTS OR APPLICATIONS

| | | |
|---|---|---|
| 218,741 | 11/1958 | Australia |
| 11,380 | 1893 | United Kingdom |

OTHER PUBLICATIONS
Chemical Abstracts, V 70, 87321x (1969).

Weidlein, J. Organometallic Chem. V 16, 33, 34 (1969).

*Primary Examiner*—Helen M. S. Sneed
*Attorney, Agent, or Firm*—Sherman & Shalloway

[57] ABSTRACT

A process for the preparation of di- or tri-substituted aluminum salts of carboxyl group-containing, pharmaceutically effective compounds which comprises reacting up to three types of carboxyl group-containing, pharmaceutically effective compounds with an organic aluminum compound expressed by the following formula;

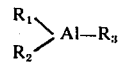

wherein $R_1$ and $R_2$, which may be the same or different, stand for an aliphatic, alicyclic or aromatic hydrocarbon residue having up to 10 carbon atoms, and $R_3$ stands for a hydrocarbon residue as defined with respect to $R_1$ and $R_2$, which may be the same as, or different from, $R_1$ and $R_2$, or a hydrocarbyloxy group of the formula $OR_4$ in which $R_4$ is an aliphatic, alicyclic or aromatic hydrocarbon residue having up to 10 carbon atoms, and a novel di- or tri-substituted aluminum salts of carboxyl group-containing, pharmaceutically effective compounds.

3 Claims, No Drawings

TRI-SUBSTITUTED ALUMINUM SALTS OR DI-SUBSTITUTED ALUMINUM SALTS OF CARBOXYL GROUP-CONTAINING, PHARMACEUTICALLY EFFECTIVE COMPOUNDS

This is a continuation of application Ser. No. 236,347, filed Mar. 20, 1972, now U.S. Pat. No. 3,865,857.

This invention relates to a novel process for preparing trisubstituted aluminum salts or di-substituted aluminum salts of carboxyl group-containing, pharmaceutically effective compounds, and to novel tri-substituted aluminum salts or di-substituted aluminum salts of carboxyl group-containing, pharmaceutically effective compounds prepared by such novel process.

A great number of carboxyl group-containing, pharmaceutically effective compounds have heretofore been known, but only a limited number of such aluminum salts are known. That is, only such compounds as monohydroxyl aluminum di-[N-3′-trifluoromethylphenyl)anthranilate], and aluminum tri-[N-(3′-trifluoromethylphenyl)anthranilate] are known. The process for preparing such aluminum salts comprises reacting the corresponding free acid or its alkali salt with aluminum hydroxide, aluminum halide or aluminum nitrate (Japanese Patent Publication No. 6200/67) or reacting the free acid or its alkali salt with an aluminum alkoxide (Japanese Patent Publication No. 25564/68).

In such conventional process for preparing aluminum salts, it takes a considerably long time to complete the reaction. For instance, it is generaly necessary to heat the reactants on a water bath for 6 hours or longer. Moreover, the resulting aluminum salt is usually obtained in the form of a mixture of various salts such as mono-salts, bis-salts and/or tris-salts, that is, the product has the disadvantage in that the purity is very low.

Still further, the known process is also disadvantageous in that, when the starting acid or salt has in the molecule a relatively weak linkage such as ester, amide, acetal and ketal linkages, during the reaction such linkage is readily cleaved or the ester-exchange reaction occurs, with the result that the intended aluminum salt is not obtained at all, or if obtained, the yield is extremely poor. In addition, such known process can yield only a monomer of the aluminum salt, and it is extremely difficult to obtain composite substituted aluminum salts of two or three carboxyl group-containing, pharmaceutically effective compounds by such known process.

As a result of extensive research carried out in this field, it has now been found that many carboxyl group-containing, pharmaceutically effective compounds that have heretofore been known react easily with an organic aluminum compound expressed by the following formula;

wherein $R_1$ and $R_2$, which may be the same or different, stand for an aliphatic, alicyclic or aromatic hydrocarbon residue having up to 10 carbon atoms, and $R_3$ stands for a hydrocarbon residue as defined with respect to $R_1$ and $R_2$, which may be the same as, or different from, $R_1$ and $R_2$, or a hydrocarbyloxy group of the formula $OR_4$ in which $R_4$ is an aliphatic, alicyclic or aromatic hydrocarbon residue having up to 10 carbon atoms, to form an aluminum salt; when the above reaction is conducted by adding the carboxyl group-containing, pharmaceutically effective compound in the form of a solution in an inert organic solvent to a solution of the organic aluminum compound expressed by formula (III) in an inert organic solvent, not only is a monomer of a di-substituted or tri-substituted simple aluminum salt of the carboxyl group-containing, pharmaceuticaly effective compound formed but also a polymer of such salt of a low degree of polymerization can readily be formed; and that when two or three carboxyl group-contaning, pharmaceutically effective compounds are added coincidentally or in succession in the above reaction, a monomer or low polymer of a di- or tri-substituted composite aluminum salt can also be formed.

In accordance with this invention, a process is provided for the preparation of aluminum salts of carboxyl group-containing, pharmaceutically effective compounds expressed by the following formula;

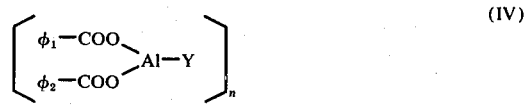

wherein Y stands for a hydroxyl group or a group $-OOC-\phi_3$; $\phi_1$, $\phi_2$ and $\phi_3$, which may be the same or different, stand for the carboxyl group-free residue of a carboxyl group-containing, pharmaceutically effective compound; and $n$ is a number of 1 or more, which comprises reacting at least one carboxyl group-containing, pharmaceutically effective compound expressed by the following formula;

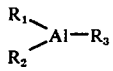

wherein $\phi$ stands for the carboxyl group-free residue of a carboxyl group-containing, pharmaceutically effective compounds, with an organic aluminum compound expressed by the following formula;

wherein $R_1$ and $R_2$, which may be the same or different, stand for an aliphatic, alicyclic or aromatic hydrocarbon residue having up to 10 carbon atoms, and $R_3$ stands for a hydrocarbon residue as defined with respect to $R_1$ and $R_2$, which may be the same as, or different from, $R_1$ and $R_2$, or a hydrocarbyloxy group of the formula $OR_4$ in which $R_4$ is an aliphatic, alicyclic or aromatic hydrocarbon residue having up to 10 carbon atoms, and, when the reaction product is a di-substituted aluminum salt of the carboxyl group-containing, pharmaceutically effective compound, hydrolyzing the same.

In the above reaction of this invention, it has also been found that when organic aluminum compounds of formula (III) are subjected under conditions for reaction with pharmaceutically effective compounds which contain in the molecule, in addition to a free carboxyl group, other active hydrogen-containing groups such as primary and secondary amino group, mercapto groups or hydroxyl groups, they react preferentially with the active hydrocarbon of the carboxyl group by dehydrocarbonation or dealcohalation, and they react secondarily with other active hydrogen-containing groups to form a complex linkage or complex compound; and that such reaction proceeds smoothly even under very mild conditions with such characteristic that even if a relatively weak linkage such as an ester, amide, acetal or ketal linkage is present, no cleavage occurs in such linkage.

In low polymers of aluminum salts of carboxyl group-containing: pharmaceutically effective compounds obtained according to the process of the present invention, if the degree of polymerization (namely, "n" in formula (IV)) is adjusted suitably, when they are administered, the pharmaceutically effective compounds contained in the low polymers are gradually released, and the pharmaceutical effect can be maintained and manifested continuously for a much longer time than in the case of administration of the pharmaceutically effective compound or monomer of the aluminum salt thereof alone. Further, in such low polymers the free carboxyl group is protected and therefore, side effects caused by the free carboxyl group, such as ulceration of stomach walls or intestinal walls, can be prevented. This is one of the prominent advantages attained by low polymers of aluminum salts of pharmaceutically effective compounds.

Furthermore, according to this invention it is possible to prepare with great ease substituted composite aluminum salts of two or three carboxyl group-containing, pharmaceutically effective compounds. Such composite aluminum salts are composite salts of two or three different pharmaceutically effective compounds; therefore, they have the following advantages.

For instance, in a composite salt of a combination of a basis and an adjuvant, synergism such as addition or potentiation can be attained, or the side effect of the basis can be reduced by the adjuvant. Further, the activity of the basis may be made gradual or immediate by selecting a suitable adjuvant to be combined with the basis. Still further, the side effect of the basis can be reduced by protecting the free carboxyl group of the basis, or it is possible to obtain the basis in a compact form suitable for administration or drug manufacture.

In the instant specification, the term "substituted simple aluminum salt" means an aluminum salt of one pharmaceutically effective compound having a carboxyl group, and the term substituted composite aluminum salt" means an aluminum salt of two or more carboxyl group-containing, pharmaceutically effective compounds. Any of the known pharmaceutically effective compounds containing a carboxyl group may be applied to the process of this invention, and converted to a di-substituted or tri-substituted aluminum salt. A great number of carboxyl group-containing, pharmaceutically effective compounds have heretofore been known, and any of them can be employed in this invention. In the instant specification, these pharmaceutically effective compounds containing a carboxyl group are expressed, as a matter of convenience, by the following formula;

    (II)

wherein $\phi$ stands for the carboxyl group-free residue of a carboxyl group-containing, pharmaceutically effective compound.

More specifically, the residue $\phi$ is selected from straight and branched alkenyl groups, substituted and unsubstituted alicyclic hydrocarbon groups, substituted and unsubstituted fused alicyclic hydrocarbon groups, substituted and unsubstituted aromatic hydrocarbon groups, and substituted and unsubstituted heterocyclic hydrocarbon groups.

Typical instances of carboxyl group-containing pharmaceutically effective compounds to be used in this invention are as follows:

1. Antipyretics, analgestics and antiphlogistics

Acetylsalicylic acid, salicylsalicylic acid, acetylsalicylsaicylic acid, salicyclic acid, N-(3'-triflurome-thylphenyl)-anthranilic acid, N-(2,3-dimethylphenyl)-anthranilic acid, p-isobutylphenyl acetic acid, p-isobutylphenyl propionic acid, 1-(p-chrolobenzoyl)-5-methoxy-2-methyl-indolyl-3-acetic acid, N-(4,5-dihydronaphth[2,1-d]isoxazolyl-3-carbonyl)-L-glutamine, 4,5-dihydronaphth[2,1-d]isoxazolyl-3-acetic acid, 7-methoxy-4,5-dihydronaphth[2,1-d]isoxazolyl-3-acetic acid, naphth[2,1-d]isoxazolyl-3-acetic acid, N-(naphth[2,1-d]isoxazolyl-3-carbonyl)-L-phenylalanine, N-(8-methoxy-naphth[2,1-d]isoxazolyl-3-carbonyl)-L-glycine, N-(7-methoxy-4,5-dihydronaphth[2,1-d]isoxazolyl-3-carbonyl)-L-glycine, N-(8-methoxy-naphth[2,1-d]isoxazolyl-3-carbonyl)-L-glycine, N-(8-methoxy-4,5-dihydronaphth[2,1-d]isoxazolyl-3-carbonyl)-alanine, N-(naphth[2,1-d]isoxazolyl-3-carbonyl-L-glycine, N-(4,5-dihydronaphth[2,1-d]isoxazolyl-3-carbonyl)-L-glycine, N-(4,5-dihydronaphth[2,1-d]isoxazolyl-3-carbonyl)-L-alanine, N-(4,5-dihydronaphth[2,1-d]isoxazolyl-3-carbonyl)-L-phenylalanine, and N-α-(4,5-dihydronaphth[2,1-d]isoxazolyl-3-carbonyl)-L-glutamine.

2. Antiulcerative agents 4,5-Dihydronaphth[1,2-c]isoxazolyl-3-carboxylic acid, N-(4,5-dihydronaphth[1,2-c]isoxazolyl-3-carbonyl)-L-glutamine, N-(naphth[1,2-c]isoxazolyl-3-carbonyl)-L-glutamine, N-(4,5-dihydronaphth[1,2-c]isoxazolyl-3-carbonyl)-L-glycine, N-(4,5-dihydronaphth[1,2-c]isoxazolyl-3-carbonyl)-L-alanine, N-(4,5-dihydronaphth[1,2-c]isoxazolyl-3-carbonyl)-lysine, N-(4,5-dihydronaphth[1,2-c]isoxazolyl-3-carbonyl)-L-leucine, N-(4,5-dihydronaphth[1,2-c]isoxazolyl-3-carbonyl)-L-serine, N-(4,5-dihydronaphth[1,2-c]isoxazolyl-3-carbonyl)-L-phenylalanine, N-(4,5-dihydronaphth[1,2-c]isoxazolyl-3-carbonyl)-L-tyrosine, and N-α-(4,5-dihydronaphth[1,2-c]isoxazolyl-3-carbonyl)-L-histidine.

3. Hypotensive agents

4-Chloro-N-(2-furylmethyl)-5-sulfamoyl-anthranilic acid.

4. Antidiarrhoics

3-Hydroxynaphthoic acid.

5. Cholagogues

Dihydrocholic acid, ursodesoxycholic acid, acid cholic acid, α-(1-hydroxy-4-phenylcyclohexyl)-butyric acid, mono-α-(5-norbornen-2-yl)ethyl succinate, and 1-methoxy-4-naphthyl-propionic acid.

6. Decholesterolizing agents

Nicotinic acid, pyridyl-3-acetic acid, linolic acid, linoleic acid, and arachidonic acid.

7. Vitamins

Orotic acid (vitamin $B_{13}$), ascorbic acid (vitamin C), and biotin (vitamin H).

8. Antileukemic agents

Amethopterin and aminopterin.

9. Antibiotics

Hydroxybenzyl penicillin (penicillin X), phenoxymethyl penicillin, heptyl penicillin, pentenyl penicillin, ampicillin, oxacillin, calbenicillin, cloxacillin, dichloroxacillin, phenethicillin, propicillin, methicillin, cephalothin and cephaloridine.

10. Hemostatics

4-Aminomethyl-cyclohexyl carboxylic acid, 4-aminoethyl-cyclohexyl carboxylic acid, and 4-aminomethyl-1,2,3,4-tetrahydronaphthoic acid, and 4-aminoethyl-1,2,3,4-tetrahydronaphthoic acid.

11. Antivirotics p-[1-(4-Phenylbenzoyl)-1-ethoxy]methylamino-benzoic acid, and 1-ethyl-4-oxo-(5,6-e)-piicolino-nicotinic acid.

12. Chemo-therapeutics p-Aminosalicylic acid.

Organic aluminum compounds of formula (III) to be used in this invention include tri-(hydrocarbyl) aluminum expressed by the following formula;

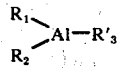  (III-1)

wherein $R_1$ and $R_2$ are as defined above in formula (III), and $R'_3$ stands for a hydrocarbon residue as defined with respect to $R_1$ and $R_2$ in formula (III), which may be the same as, or different from, $R_1$ and $R_2$, and di-(hydrocarbyl)-mono-(hydrocarbyloxy) aluminum expressed by the following formula;

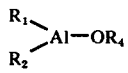  (III-2)

wherein $R_1$, $R_2$ and $R_4$ are as defined above in formula (III).

Preferred examples of $R_1$, $R_2$ and $R'_3$ in formulae (III-1) and (III-2) are straight and branched alkyl groups of 2 to 5 carbon atos, cycloalkyl groups of 5 to 7 carbon atoms, and phenyl and benzyl groups. As such alkyl group ethyl, n-propyl, isopropyl, n-butyl, isobutyl, n-amyl, isoamyl and sce-amyl groups may be mentioned. As the cycloalkyl group cyclohexyl and cycloheptyl groups may be exemplified. Among these groups, alkyl groups have the highest reactivity with the pharmaceutically effective compound expressed by formula (II), and among the alkyl groups, one having a smaller number of carbon atoms exhibits a higher reactivity with the pharmaceutically effective compound of formula (III).

Examples of the organic aluminum compound expressed by formula (III-1) are triethyl aluminum, tripropyl aluminum, triisobutyl aluminum, triphenyl aluminum, diethylpropyl aluminum, diethylbutyl aluminum and triamyl aluminum.

Preferable examples of the $R_4$ group in formula (III-2) are straight and branched alkyl groups of 2 to 5 carbon atoms, such as ethyl, n-propyl, isopropyl, n-butyl, isobutyl, n-amyl, isoamyl and sec-amyl. Since the alkoxy group ($-OR_4$) is much lower than alkyl, cycloalkyl, phenyl and benzyl groups as $R_1$, $R_2$ and $R'_3$, with respect to the reactivity with the pharmaceutically effective compound of formula (II), the organic aluminum compounds expressed by formula (III-2) are especially suitable for synthesis of di-substituted aluminum salts. Specific examples of the organic aluminum compound of formula (III-2) are diethylethoxy aluminum, diethylisopropoxy aluminum, dipropylisopropoxy aluminum, di-isobutylethoxy aluminum, and diethylphenoxy aluminum.

In the practice of the process of this invention there is no substantial difference between preparation of simple aluminum salts and composite aluminum salts of carboxyl group-containing, pharmaceutically effective compounds. Namely, in the process of this invention, the intended objects can be accomplished by adding a carboxyl group-containing, pharmaceutically effective compound of formula (II) in the form of a solution in an inert organic solvent to a solution of an organic aluminum compound of formula (III) in an inert organic solvent, and reacting them, preferably under anhydrous conditions. In the case of preparation of the composite aluminum salts, special care must be paid to the order of addition of the reactants.

In the process of this invention, a solution of an organic aluminum compound of formula (III-1) or (III-2) in an inert organic solvent is first prepared. As such inert organic solvent saturated hydrocarbons such as n-pentane, n-hexane, n-heptane and petroleum ether; alicyclic hydrocarbons such as cyclopentane, cyclohexane and decalin: aromatic hydrocarbons such as benzene, toluene, xylene and tetralin; ethers such as tetrahydrofuran, dioxane diethylene glycoldimethylether and dimethoxyethane; esters such as ethyl acetate, butyl acetate, amyl acetate and ethyl propionate; amides such as dimethyl formamide and dimethyl acetamide; and ketones such as acetone and methylethylketone may be employed.

These solvents should be inert either to the organic aluminum compound and also to any of the carboxyl group-containing, pharmaceutically effective compounds to be used in the reaction.

When preparation of a tri-substituted or di-substituted, simple aluminum salt of the carboxyl group-containing, pharmaceutically effective compound is intended, to the so-prepared inert organic solvent solution of the organic aluminum compound of formula (III-1) or (III-2) a solution of the pharmaceutically effective compound in an inert organic solvent which is identical or compatible with the solvent used for preparaion of the solution of the organic aluminum compound is added, and they are mixed under agitation, or the above order of addition may reversed; that is, the inert organic solvent solution of the organic aluminum compound is added to the inert organic solvent solution of the carboxyl group-containing, pharmaceutically effective compound. In view of ease in control of the reaction heat, it is preferred to gradually add the inert organic solvent solution of the organic aluminum compound to the inert organic solvent solution of the pharmaceutically effective compound.

In this reaction, when 3 moles or slightly more than 3 moles of the carboxyl group-containing, pharmaceutically effective compound are used per mole of the organic aluminum compound, a tri-substituted aluminum salt or its low polymer of the following formula;

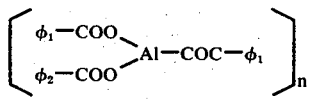
(IV-1)

is formed. When about 2 moles of the pharmaceutically compound are reacted per mole of the organic aluminum compound, di-substituted aluminum salt or its low polymer of the following formula is formed;

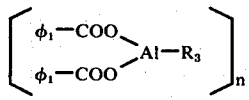
(IV-2)

The so formed di-substituted aluminum salt or its low polymer can be easily converted to a basic di-substituted aluminum salt or its low polymer of the following formula;

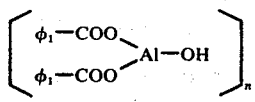
(IV-3)

when the resulting reaction mixture is hydrolyzed by addition of water or by action of moisture in the air.

When two or three carboxyl group-containing, pharmaceutically effective compounds are used in the reaction in order to produce a di-substituted or tri-substituted composite aluminum salt thereof, as described above, special care must be paid to the order of addition of the reactants. To the inert organic solvent solution of the organic aluminum compound prepared by the above-mentioned method inert organic solvent solutions of two or three pharmaceutically effective compounds containing a carboxyl group are added coincidentally or successively. It is preferred to effect the addition of solutions of the pharmaceutically effective compounds successively. When the order of the addition is reversed, that is, the inert organic solvent solution of the organic aluminum compound is added to solutions of the hydroxyl group-containing, pharmaceutically effective compounds, a mixture of various tri-substituted or di-substituted simple salts of two or three pharmaceutically effective compounds, or various tri-substituted or di-substituted composite aluminum salts of the pharmaceutically effective compounds is formed. Accordingly, such manner of addition is not preferred. The total amount of the two or three carboxyl group-containing, pharmaceutically effective compounds to be added may be 2 moles or slightly more than 2 moles per mole of the organic aluminum compound. For instance, when the process of this invention is conducted with the use of 1 mole each of two pharmaceutically effective compounds ($\phi'_1$—COOH and $\phi'_2$—COOH) per mole of the organic aluminum compound, a di-substituted composite aluminum salt or its low polymer expressed by the following formula is formed;

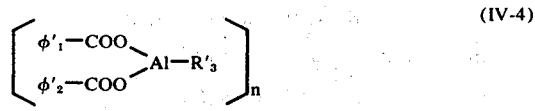
(IV-4)

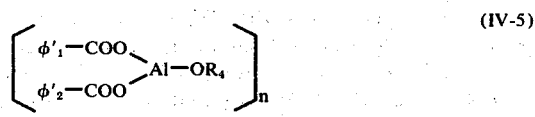
(IV-5)

In the above formulas and formulas given below, $\phi'_1$, $\phi_2$ and $\phi_3$, which are different from each other, stand for the carboxyl group-free residue of the carboxyl group-containing, pharmaceutically effective compound.

The reaction product expressed by above formula (IV-4) or (IV-5) is hydrolyzed by addition of water or by adtion of moisture in the air to another form of the intended product of this invention, namely a basic, di-substituted composite aluminum salt of the following formula;

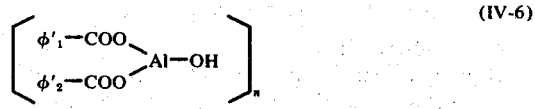
(IV-6)

In another embodiment of this invention, about 2 moles of one pharmaceutically effective compound ($\phi'_1$—COOH) and about 1 mole of another pharmaceutically effective compound ($\phi'_2$—COOH), or about 3 moles or slightly more than 3 moles of an equimolar mixture of three different pharmaceutically effective compounds ($\phi'_1$—COOH, $\phi'_2$—COOH and $\phi'_3$—COOH) are reacted with one mole of the organic aluminum compound of formula (III-1) or (III-2). As a result, a tri-substituted composite aluminum salt or its low polymer expressed by the following formula is obtained;

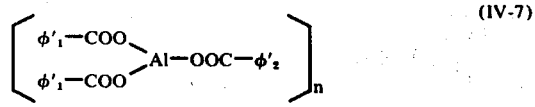
(IV-7)

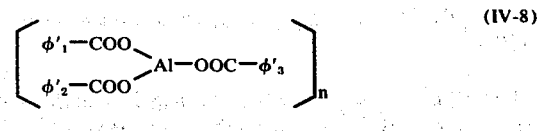
(IV-8)

in which, as is seen from the above formulae, two or three pharmaceutically effective compounds are combined as substituents.

In some of the pharmaceutically effective compounds having, in addition to the carboxyl group, other active hydrogen atom-containing groups such as hydroxyl and amino groups, these active hydrogen-containing groups form a complex linkage at the same time that the carboxyl group forms an aluminum salt. For instance, when p-amino-salicylic acid is used as the pharmaceutically effective compound, either the amino group or hydroxyl group forms a complex linkage coincidentally with the reaction of the carboxyl group, which results in formation of aluminum bis(4-amino-2-hydroxybenzoate).

The salt-forming reaction between one or a plurality of carboxyl group-containing, pharmaceutically effective compounds and the organic aluminum compound expressed by formula (III-1) or (III-2) is generally carried out in an atmosphere of an inert gas such as nitrogen, argon and helium. In this salt-forming reaction, the dehydrocarbonation between the hydrocarbon residue bonded to the aluminum atom and the active hydrogen atom of the carboxyl group of the pharmaceutically effective compound is first allowed to advance preferentially. The dealcoholation between the alkoxy group of the organic aluminum compound expressed by formula (III-2) and the active hydrogen atom of the carboxyl group is not so vigorous as the above-mentioned dehydrocarbonation. Accordingly, higher temperatures are adopted in the dealcoholation than in the above dehydrocarbonation. Therefore, when formation of a di-substituted aluminum slt is wanted, it is preferred to employ an organic aluminum compound of formula (III-2) rather than an organic aluminum compound of formula (III-1).

The formation of a di-substituted aluminum salt by the dehydrocarbonation between the pharmaceutically effective compound and the tri-(hydrocarbyl) aluminum or by the dealcoholation between the pharmaceutically effective compound and the di-(hydrocarbyl)-mono-(hydrocarbyloxy) aluminum is accomplished by agitating and mixing both the reactants in an inert organic solvent, preferably while keeping the reactants in the state dissolved in the solvent, under cold conditions or even at temperatures exceeding the boiling point of the solvent, for instance, at temperatures, ranging from $-50°$ C. to 60° C., preferably from 30° C. to room temperature for a period ranging from 10 minutes to 24 hours, preferably from 1 to 3 hours. The formation of an aluminum salt by the dealcoholation between the hydrocarbyloxy group (preferably an alkoxy group of 2 – 5 carbon atoms) of the organic aluminum compound of formula (III-2) and the active hydrocarbon atom of the carboxyl group of the pharmaceutically effective compound can be accomplished by agitating and mixing both the reactants in an inert organic solvent, preferably while keeping them in the state dissolved in the solvent, at relatively high temperatures, for instance, at temperatures exceeding 50° C., preferably from 80° C. to 150° C., particularly preferably from 90° C. to 120° C., for a period of from 1 to 3 hours. This reaction may be carried out in a dry atmosphere.

When an inert organic solvent solution of one pharmaceutically effective compound having a carboxyl group is added to a solution of the organic aluminum compound in an inert organic solvent according to this invention, a salt is formed between them by the above-mentioned dehydrocarbonation reaction. Accordingly, if the pharmaceutically effective compound is added in an amount of about 1 mole per mole of the organic aluminum compound, a mono-substituted aluminum salt is formed. When the amount of the pharmaceutically effective compound is increased to about 2 moles per mole of the organic aluminum compound, a di-substituted aluminum salt expressed by formula (IV-2) is formed, and when another 1 mole of the pharmaceutically effective compound is further added, a tri-substituted simple salt expressed by formula (IV-1) is formed.

It is possible to obtain a di-substituted composite aluminum salt expressed by formula (IV-4) or (IV-6) or a tri-substituted aluminum composite salt expressed by formula (IV-7) by adding to the above reaction mixture including the mono-substituted aluminum salt or di-substituted simple aluminum salt a different kind of carboxyl group containing, pharmaceutically effective compound in an amount of about 1 mole per mole of the organic aluminum compound. If desired, it is possible to form a composite aluminum salt of formula (IV-8) substituted by three different pharmaceutically effective compounds by adding to the reaction mixture including the di-substituted aluminum salt of formula (IV-4) or (IV-6) another kind of carboxyl group-containing, pharmaceutically effective compound in an amount of about 1 mole per mole of the organic aluminum compound and reacting them.

According to this invention, as described above, when two or three different pharmaceutically effective compounds containing a carboxyl group are reacted successively with the above-mentioned organic aluminum compound in an inert organic solvent, it is possible to obtain a desired substituted composite aluminum salt while controlling the kind and number of the pharmaceutically effective compounds participating in the salt formation.

Of course, as described hereinabove, it is also possible to form a di-substituted aluminum salt and then convert it to a basic di-substituted aluminum salt by hydrolysis of the once formed di-substituted salt.

This hydrolysis can be accomplished very easily by a customary method, for instance, by adding water to the reaction mixture containing the di-substituted aluminum salt.

The above-mentioned salt formation may also be accomplished by coincidental addition of two or three pharmaceutically effective compounds containing a carboxyl group instead of the above-mentioned successive addition of them. In this case, each of the pharmaceutically effective compounds is added at the above-mentioned molar ratio, and the total amount thereof is adjusted to 2 moles or slightly more than 2 moles, or 3 moles or slightly more than 3 moles, per mole of the organic aluminum compound.

By the above-mentioned procedures, reaction product substituted by desired pharmaceutically effective compounds at a desired ratio, namely a desired substituted composite aluminum salt can be obtained.

In connection with inert organic solvents to be used for the above reaction of this invention, the solvent for dissolving the organic aluminum compound is identical, or compatible or incompatible, with the solvent for dissolving the pharmaceutically effective compound containing a carboxyl group.

The tri-substituted aluminum salt or di-substituted basic aluminum salt formed by the above-mentioned process of this invention can be separated from the solvent in the reaction mixture by a customary method, for instance, by filtration, centrifugal separation, solvent distillation, drying under reduced pressure or the like. If desired, the recovered salt may be purified by recrystallization, reprecipitation or the like.

In accordance with this invention, the tri-substituted aluminum salt or di-substituted aluminum salt of the carboxyl group-containing pharmaceutically effective compound is obtained in the form of either a monomer expressed by the following formula;

or a polymer of a low degree of polymerization in which two or more aluminum salt monomers of formula (V) are polymerized through the coordination bond which is expressed by the following average formula;

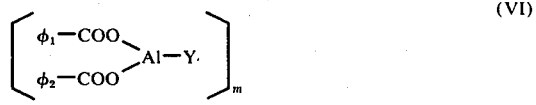

wherein $m$ is a number greater than 1 (not limited to an integer).

In the instant specification, the degree of polymerization ($n$ or $m$) of the aluminum salt polymer is an average degree of polymerization calculated from the value of the average molecular weight determined by the vapor pressure osmoscopic method.

The degree of polymerization of the low polymer of the aluminum salt expressed by formula (VI) can be easily controlled by adjusting the conditions for formation of the aluminum salt, especially the reaction temperature, the reaction time and the kind of solvent appropriately. For instance, when the reaction is carried out at such a low temperature as ranging from $-30°$ C. to $0°$ C., for a relatively short period, a monomer of formula (V) or a polymer of a lower degree of polymerization of formula (VI) in which the value of $m$ is about 1.1 is obtained. On the other hand, when the reaction is effected at a relatively high temperature such as ranging from $50°$ C. to $60°$ C. for a relatively long time, a polymer of a relatively high degree of polymerization in which $m$ in formula (VI) is 5 or more is obtained.

The average degree of polymerization may also be controlled by selecting the reaction solvent suitably. For instance, the use of an aromatic hydrocarbon such as benzene and toluene tends to give a product of a high degree of polymerization, whereas the use of an ether such as ethyl ether, dimethoxyethane and tetrahydrofuran tends to result in formation of a polymer of a low degree of polymerization or a monomer. In order to prepare an aluminum salt having a degree of polymerization suitable for medicine, it is preferred to employ the latter solvent, i.e., ethers.

Furthermore, in order to adjust the degree of polymerization of the resulting aluminum salt within a desired range, it is possible in this invention to employ customary agents for regulating the degree of polymerization.

Thus, in accordance with this invention it is possible to obtain not only a low polymer of an aluminum salt such as one having an average degree of polymerization of about 1.1 but also a polymer having such a relatively high degree of polymerization of up to 50 or more.

However, polymers having an average degree of polymerization of about 10 or less, preferably about 5 or less, especially preferably from 1.1 to 1.5, are desired.

Tri-substituted simple aluminum salts and di-substituted simple aluminum salts of formulae (IV-1) and (IV-3) prepared according to the novel process of this invention are novel compounds except only a few of them; that is, except aluminum tris[2-N-(3-trifluoromethylphenyl)anthranilate], mono-hydroxy aluminum bis-[2-N-(3-trifluoromethylphenyl)anthranilate], mono-hydroxy aluminum bis-(acetylsalicylate), a di-substituted basic simple aluminum salt of ampicillin, tri-substituted basic simple aluminum salts and di-substituted basic simple and aluminum salts of substituted and unsubstituted naphth[2,1-d]isoxazolyl-3-ethanoic acids, and tri-substituted simple aluminum salts and di-substituted basic simple aluminum salts of substituted and unsubstituted naphth[1,2-c]isozazolyl-3-acetic acids. (Each of these known aluminum salts takes only a monomer form.)

Further, tri-substituted composite aluminum salts and di-substituted basic simple aluminum salts of formulae (IV-6), (IV-7) and (IV-8) are novel compounds synthesized for the first time according to this invention by employing an organic aluminum compound having a peculiar and characteristic reactivity.

Accordingly, this invention provides novel tri-substituted aluminum salts of carboxyl group-containing, pharmaceutically effective compounds expressed by the following formula:

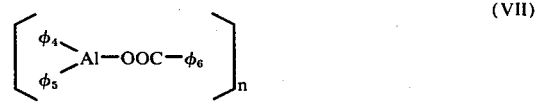

wherein $\phi_4$, $\phi_5$ and $\phi_6$, which may be the same or different, stand for the carboxyl group-free residue of a carboxyl group-containing, pharmaceutically effective compound, and $n$ is a number of 1 or more, with the proviso that when $n$ is 1, all of $\phi_4$, $\phi_5$ and $\phi_6$ should not coincidentally be a 2-N-(3'-trifluoromethylphenyl)-aminophenyl group, or a substituted or unsubstituted naphth[2,1-d]isoxazolyl-3-methyl or 3-naphth[1,2-c]ospxazolyl group, and novel di-substituted basic aluminum salts of carboxyl group-containing, pharmaceutically effective compounds expressed by the following formula:

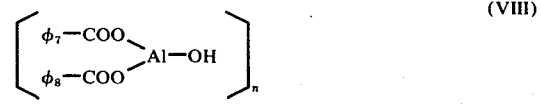

wherein $\phi_7$ and $\phi_8$, which may be the same or different, stand for the carboxyl group-free residue of a carboxyl group-containing pharmaceutically effective compound, and $n$ is a number of 1 or more, with the proviso that when $n$ is 1, both of $\phi_7$ and $\phi_8$ should not coincidentally be a 2-acetoxyphenyl group, a 2-N-(3'-trifluoromethylphenyl)-aminophenyl group, an ampicillin residue, or a substituted or unsubstituted naphth[2,1-d]isoxazolyl-3-methyl or 3-naphth[1,2-c]isoxazolyl group.

In above formula (VII) and (VIII), $n$ is a number of 1 or more, preferably up to 10. In view of the absorbing effect and the activity durability in the application of aluminum salts of this invention, it is especially preferred that $n$ is within a range of from 1 to 1.5.

In illustration of this invention, examples of tri-substituted aluminum salts and di-substituted basic aluminum salts expressed by above formulae (VII) and (VIII) are given hereinbelow.

1. Tri-substituted simple aluminum salts
   aluminum tris-(acetylsalicylate).
   aluminum tris-(salicylsalicylate),
   aluminum tris-(acetylsalicylsalicylate),
   aluminum tris-salicylate,
   aluminum tris-(p-isobutylphenylacetate),
   aluminum tris-(p-isobutylphenylpropionate),
   aluminum tris-[1-(p-chlorobenzoyl)-5-methoxy-2-methyl-3-indolyl-acetate],
   aluminum tris-[4-chloro-N-(2-furylmethyl)-5-sulfamoylanthranilate],
   aluminum tris-(3-hydroxy-2-naphthoate),
   aluminum tris(dehydrochlate),
   aluminum tris-(ursodesoxycholate),
   aluminum tris-(1-methoxy-4-naphthylpropionate),
   aluminum tris-nicotinate,
   aluminum tris-(pyridyl-3-acetate),
   aluminum tris-[6-(phenoxymethylcarbamoyl)-penicillanate],
   aluminum tris-(4-aminomethyl-cyclohexylcarboxylate),
   aluminum tris-(4-aminomethyl-1,2,3,4-tetrahydronaphthocarboxylate),
   aluminum tris-(4-aminoethyl-1,2,3,4-tetrahydronaphthocarboxylate),
   aluminum tris-(p-aminosalicylate),
   aluminum tris-{N-(naphth[2,1-d]isoxazolyl-3-carbonyl)-L-glycinate},
   aluminum tris-{N-(4,5-dihydronaphth[2,1-d]isoxazolyl-3-carbonyl)-L-glycinate}, and
   low polymers of these salts.
2. Tri-substituted composite aluminum salts
   aluminum mono-flufenamate mono-acetylsalicylate mono-isonicotinate,
   aluminum mono-(p-aminosalicylate) mono-acetylsalicylate mono-isonicotinate,
   aluminum mono-(p-aminosalicylate) mono-acetylsalicylate mono-(4,5-dihydronaphth[2,1-d]isoxazolyl-ethanoate),
   aluminum mono-[1-(p-chlorobenzoyl)-5-methoxy-2-methyl-3-indolyl-acetate]bis-acetylsalicylate,
   aluminum mono-acetylsalicylate bis-[1-(p-chlorobenzoyl)-5-methoxy-2-methyl-3-indolylacetate],
   aluminum mono-nicotinate bis-acetylsalicylate,
   aluminum mono-orotate bis-acetylsalicylate,
   aluminum mono-(p-aminosalicylate) bis-[6-{4-(3-phenyl-5-methyloxazolyl)-carbamoyl}penicillanate],
   aluminum mono-acetylsalicylate bis[6-{1-(2,6-dimethoxyphenyl)-carbamoyl}penicillanate],
   aluminum mono-acetylsalicylate bis-[N-(3-trifluoromethyl)-anthranilate],
   aluminum mono-acetylsalicylate bis-[N-(2,3-dimethylphenyl)-anthranilate],
   aluminum mono-acetylsalicylate bis-(p-isobutylphenylacetate),
   aluminum mono-acetylsalicylate bis-(p-isobutylphenylpropionate),
   aluminum mono-acetylsalicylate bis-(naphth[2,1-d]isoxazolyl-3-acetate),
   aluminum mono-acetylsalicylate bis-(4,5-dihydronaphth[2,1-d]isoxazolyl-3-acetate),
   aluminum mono-acetylsalicylate bis-(4,5-dihydronaphth[2,1-d]isoxazolyl-3-carbonyl-L-glycinate),
   aluminum mono-acetylsalicylate bis-(4,5-dihydronaphth[1,2-c]isoxazolyl-3-carbonate),
   aluminum mono-acetylsalicylate bis-(4,5-dihydronaphth[1,2-c]isoxazolyl-3-carbonyl-L-glycinate),
   aluminum mono-acetylsalicylate bis-(p-aminosalicylate),
   aluminum mono-[1-ethyl-4-oxo-(5,6-e)-picolinonicotinate] bis-[6-{4-(3-phenyl-5-methyloxazolyl)-carbamoyl}penicillanate],
   aluminum mono-[4-chloro-N-(2-furylmethyl)-5-sulfamoylanthranilate]bis-linolenate, and
   low polymers of these salts.

3. Di-substituted basic simple aluminum salts
   monohydroxy aluminum bis-salicylsalicylate,
   monohydroxy aluminum bis-acetylsalicylsalicylate,
   monohydroxy aluminum bis-salicylate,
   monohydroxy aluminum bis-(p-isobutylphenyl-acetate),
   monohydroxy aluminum bis-(p-isobutylphenyl-propionate),
   monohydroxy aluminum bis-[1-(p-chlorobenzoyl)-5-methoxy-2-methyl-3-indolyl-acetate],
   monohydroxy aluminum bis-(3-hydroxy-2-naphthoate),
   monohydroxy aluminum bis-(1-methoxy-4-naphthylpropionate),
   monohydroxy aluminum bis-(p-aminosalicylate),
   monohydroxy aluminum bis-(4-aminomethyl-1,2,3,4-tetrahydronaphthiocarbonate),
   monohydroxy aluminum bis-acetylsalicylate, and
   low polymers of these salts.

4. Di-substituted basic composite aluminum salts
   monohydroxy aluminum mono-acetylsalicylate mono-[N-(3-trifluoromethylphenyl)anthranilate],
   monohydroxy aluminum mono-(p-aminosalicylate) monoacetylsalicylate,
   monohydroxy aluminum mono-(4,5-dihydronaphth[2,1-d]isoxazolyl-3-ethanoate) mono-acetylsalicylate, and
   low polymers of these salts.

Tri-substituted aluminum salts and di-substituted aluminum salts of carboxyl group-containing, pharmaceutically effective compounds according to this invention may be formed into preparations suitable for oral administration by customary methods. For instance, they may readily be formed into tablets, powders, granules, syrups and the like. As diluents talc, lactose, starch, tragacanth gum, magnesia, gelatine, water, fructose and the like may be employed.

This invention will now be illustrated in more detail by reference to examples. In each example the molecular weight was determined according to the vapor pressure osmoscopic method by employing a molecular weight-measuring apparatus (of the Perkin-Elmer type manufacture by Hidachi). In some cases, since the aluminum salt contained conjugated water or a slight amount of the solvent was left in the recovered salt, the measured value of the molecular weight differed from the calculated value to some extent.

EXAMPLE 1

28 g of N-(3'-trifluoromethylphenyl)-anthranilic acid were added into 100 ml of dried benzene, and dried nitrogen gas was introduced thereinto. Separately, a solution of 4 g of triethyl aluminum dissolved in 50 ml of dried benzene was prepared, and this solution was added to the above benzene solution under agitation. Then, the temperature of the mixture was elevated to 50° – 60° C. to complete the reaction. After a while, a small quantity of water was carefully added to the reaction mixture. The resulting precipitate was recovered by filtration and washed with methanol. Thus, 24 g of purely white aluminum tris-[N-(3'-trifluoromethylphenyl)-anthranilate] were obtained. The molecular weight of the resulting aluminum salt was about 1,300 and the average degree of polymerization was found to be about 1.5. The infrared absorption spectrum of the salt was as follows:

$IR_{KBr}cm^{-1}$ : 3330, 1580, 1510, 1460, 1415, 1335, 1290, 1165, 1130, 1070, 755, 700

EXAMPLE 2

28 g of N-(3'-trifluoromethylphenyl)-anthranilic acid were added into 100 ml of dried benzene, and dried nitrogen gas was introduced thereinto. Separately, a solution of 4 g of triethyl aluminum dissolved in 50 ml of dried benzene was prepared, and this solution was added to the above benzene solution under agitation. After a while, a small quantity of water was carefully added to the reaction mixture. The resulting precipitate was recovered by filtration and washed with methanol. Thus, 19 g of purely white aluminum tris-(N-(3'-trifluoromethylphenyl)-anthranilate] were obtained. The molecular weight of the resulting aluminum salt was about 1200, and the average degree of polymerization was found to be about 1.4 The infrared absorption spectrum of the salt was as follows:

$IR_{KBr}cm^{-1}$ : 3300, 1580, 1510, 1460, 1415, 1335, 1290, 1165, 1130, 1070, 755, 700

EXAMPLE 3

28 g of N-(3'-trifluoromethylphenyl)-anthranilic acid were added into 100 ml of dried benzene and maintained at 15° C., and dried nitrogen gas was introduced thereinto. Separately, a solution of 4 g of triethyl aluminum dissolved in 50 ml of dried benzene was prepared, and this solution was added to the above benzene solution under agitation. After a while, a small quantity of water was added carefully to the reaction mixture, and the resulting crude precipitate was recovered by filtration and washed with methanol. Thus, 15 g of purely white aluminum tris-[N-(3'-trifluoromethylphenyl)-anthranilate] were obtained. The molecular weight of the resulting aluminum salt was about 1130, and the average degree of polymerization was found to be about 1.3. The infrared absorption spectrum of the salt was as follows:

$IR_{KBr}cm^{-1}$ : 3330, 1580, 1510, 1460, 1415, 1335, 1290, 1165, 1130, 1070, 755, 700

EXAMPLE 4

28 g of N-(3'-trifluoromethylpheny)-anthranilic acid were added into 50 ml of dried tetrahydrofuran and maintained at room temperature, and dried nitrogen gas was introduced thereinto. Separately, a solution of 4 g of triethyl aluminum dissolved in 50 ml of dried tetrahydrofuran was prepared, and this solution was added to the above tetrahydrofuran solution under agitation. After a while, the reaction mixture was thrown into a great quantity of water. The resulting crude precipitate was recovered by filtration and air-dried. Thus, 27.9 g of pearl yellow aluminum tris-[N-(3'-trifluoromethylphenyl)-anthranilate] were obtained. The resulting aluminum salt had a molecular weight of about 950, and the average degree of polymerization was found to be about 1.1. The infrared absorption spectrum of the salt was as follows :

$IR_{KBr}cm^{-1}$ : 3330, 1580, 1510, 1460, 1415, 1335, 1290, 1165, 1130, 1070, 755, 700

EXAMPLE 5

28 g of N-(3'-trifluoromethylphenyl)-anthranilic acid were added into 50 ml of dried tetrahydrofuran and maintained at 0°C., and dried nitrogen gas was introduced thereinto. Separately, a solution of 4 g of triethyl aluminum dissolved in 50 ml of dried tetrahydrofuran was prepared, and this solution was added to the above tetrahydrofuran solution under agitation. After a while, the reaction mixture was thrown into a great quantity of water. The resulting crude precipitate was recovered by filtration and dried under reduced pressure. Thus, 27 g of pearl yellow aluminum tris-[N-(3'-trifluoromethylphenyl)-anthranilate] were obtained. The resulting aluminum salt has a molecular weight of about 880, and the average degree of polymerization was found to be about 1. The infrared absorption spectrum of the salt was as follows :

$IR_{KBr}cm^{-1}$ : 3330, 1580, 1510, 1460, 1415, 1335, 1290, 1165, 1130, 1070, 755, 700

EXAMPLE 6

28 g of N-(3'-trifluoromethylphenyl)-anthranic acid were added into 100 ml of dried dimethoxyethane and maintained at −20° to −30° C., and dried nitrogen gas was introduced thereinto. Separately, a solution of 4 g of triethyl aluminum dissolved in 50 ml of dried dimethoxyethane was prepared and this solution was added to the above dimethoxyethane solution under agitation. After a while, the reaction mixture was thrown into a great quantity of water, and the resulting crude precipitate was recovered by filtration and dried under reduced pressure. Thus, 28 g of pearl yellow aluminum tris-[N-(3'-trifluoromethylphenyl)-anthranilate] were obtained. The resulting aluminum salt had a molecular weight of about 860, and the average degree of polymerization was found to be about 1. The infrared absorption spectrum of the salt was as follows :

$IR_{KBr}cm^{-1}$ : 3330, 1580, 1510, 1460, 1415, 1335, 1290, 1165, 1130, 1070, 755, 700

EXAMPLE 7

28 g of N-(3'-trifluoromethylphenyl)-anthranic acid were added into 100 ml of dried tetrahydrofuran and maintained at 15° C., and dried nitrogen gas was introduced thereinto. Separately, a solution of 4 g of triethyl aluminum dissolved in 50 ml of dried tetrahydrofuran was prepared, and this solution was added to the above tetrahydrofuran solution under agitation. After a while, a small quantity of water was carefully added to the reaction mixture and it was concentrated under reduced pressure. The resulting crude precipitate was recovered by filtration and dried under reduced pressure. Thus, 26 g of pearl yellow aluminum tris-[N-(3'-trifluoromethylphenyl)-anthranilate] were obtained. The resulting aluminum salt had a molecular weight of about 905, and the average degree of polymerization was found to be about 1.1. The infrared absorption spectrum of the salt was as follows:

$IR_{KBr} cm^{-1}$ : 3330, 1580, 1510, 1460, 1415, 1335, 1290, 1165, 1130, 1070, 755, 700

EXAMPLE 8

28 g of N-(3'-trifluoromethylphenyl)-anthranilic acid were added into 100 ml of dried dimethoxyethane and maintained at 5° C., and dried nitrogen gas was introduced thereinto. Separately, a solution of 7 g of tri-isobutyl aluminum in 50 ml of dried dimethoxyethane was prepared, and this solution was added to the above dimethoxyethane solution under agitation. After a while, the reaction mixture was thrown into a great quantity of water, and the resulting crude precipitate was recovered by filtration and air-dried. Thus, 27 g of pearl yellow aluminum tris-[N-(3'-trifluoromethylphenyl)-anthranilate] were obtained. The resulting aluminum salt had a molecular weight of about 795, and the average degree of polymerization was found to be about 1. The infrared absorption spectrum of the salt was as follows:

$IR_{KBr} cm^{-1}$ : 3330, 1580, 1510, 1460, 1415, 1335, 1290, 1165, 1130, 1070, 755, 700

EXAMPLE 9

28 g of N-(3'-trifluoromethylphenyl)-anthranilic acid were added into 100 ml of dried benzene, and the solution was treated with dried nitrogen gas. Separately, a solution of 7 g of tri-isobutyl aluminum dissolved in 50 ml of dried benzene was prepared, and this solution was added to the above benzene solution under agitation. Then, the temperature of the mixture was elevated to 60° C. by heating, and the reaction mixture was treated in the same manner as in Example 1 to 22 g of aluminum tris-[N-(3'-trifluoromethylphenyl)-anthranilate] which had a molecular weight of about 1100 and an average degree of polymerization of about 1.3.

EXAMPLE 10

Procedures of Example 1 were repeated by employing 24 g of N-(2',3'-dimethylphenyl)-anthranilic acid and 4 g of triethyl aluminum. Thus, 22 g of aluminum tris-[N-(2',3'-dimethylphenyl)-anthranilate] having a molecular weight of about 1100 and an average degree of polymerization of about 1.5 were obtained.

EXAMPLE 11

Procedures of Example 6 were repeated by employing 24 g of N-(2',3'-dimethylphenyl)-anthranilic acid and 4 g of triethyl aluminum. As a result, 23 g of pearl yellow aluminum tris-[N-(2',3'-dimethylphenyl)-anthranilate] having a molecular weight of about 760 and an average degree of polymerization of about 1 were obtained.

EXAMPLE 12

Procedures of Example 8 were repeated by employing 24 g of N-(2',3'-dimethylphenyl)-anthranilic acid and 7 of tri-isobutyl aluminum. As a result, 23 g of pearl yellow aluminum tris-[N-(2',3'-dimethylphenyl)-anthranilate] having a molecular weight of about 705 and an average degree of polymerization of about 1 were obtained.

EXAMPLE 13

3.96 g of tri-isobutyl aluminum were dissolved in 150 ml of benzene, and a solution of 10.8 g of o-acetoxybenzoic acid dissolved in 200 ml of benzene was added dropwise little by little under ice cooling to the above solution under nitrogen gas current. After completion of the dropwise addition, the temperature of the mixture was returned to room temperature, and the reaction was further continued for 2 hours under agitation. Then, the benzene was distilled off under reduced pressure. Thus, 10.1 g of aluminum tris-(o-acetoxybenzoate) having a melting point above 136° C. were obtained. The resulting aluminum salt had a molecular weight of about 790, and the average degree of polymerization was found to be about 1.4. The infrared absorption spectrum of the salt was as follows:

IR $\nu$ max $cm^{-1}$ : 1760 (—OCOCH$_3$); 1605 (—COO$^-$).

EXAMPLE 14

3.96 g of tri-isobutyl aluminum were added into 50 ml of tetrahydrofuran and the solution was cooled to 0° C. under nitrogen gas current, a solution of 10.8 g of o-acetoxybenzoic acid dissolved in 100 ml of tetrahydrofuran was added dropwise little by little to the above solution. After completion of the dropwise addition, the reaction mixture was treated in the same manner as in Example 5, followed by drying under reduced pressure. Thus, 10 g of white aluminum tris-(o-acetoxybenzoate) were obtained. The resulting aluminum salt had a molecular weight of about 570, and the average degree of polymerization was found to be about 1. The infrared absorption spectrum of the salt was as follows:

IR $\nu$ max $cm^{-1}$ : 1760 (—OCOCH$_3$); 1605 (—COO$^-$).

EXAMPLE 15

3.8 g of triethyl aluminum were dissolved in 100 ml of dimethoxyethane, and the solution was cooled to −5° C. Under nitrogen gas current, a solution of 10.8 g of o-acetoxybenzoic acid dissolved in 100 ml of dimethoxyethane was added dropwise little by little to the above solution. After completion of the dropwise addition, the temperature of the mixture was returned to room temperature, and the reaction mixture was thrown into a great quantity of water. The precipitated crude crystals were recovered by filtration and dried under reduced pressure to yield 10.5 g of white aluminum tris-(o-acetoxybenzoate) having a molecular weight of about 550 and an average degree of polymerization of about 1. The infrared absorption spectrum of the resulting aluminum salt was as follows:

IR $\nu$ max $cm^{-1}$ : 1760 (—OCOCH$_3$); 1605 (—COO$^-$).

EXAMPLE 16

3.96 g of tru-isobutyl aluminum were dissolved in 150 ml of benzene and the solution was maintained at 40° C. Under nitrogen gas current, a solution of 7.2 g of o-acetoxybenzoic acid dissolved in 100 ml of tetrahydrofuran was added dropwise little by little to the above solution. After completion of the dropwise addition, the temperature of the mixture was returned to room temperature and the reaction was further continued for 2 hours under agitation. Then, 10 ml of water were added to the reaction mixture and the reaction was carried out for another 1 hour. After completion of the reaction, the solvent was distilled off. The residue was thrown into water, and the precipitated powder was recovered by filtration. As a result, 7.0 g of monohydroxy aluminum bis-(o-acetoxybenzoate) having a molecular weight of about 850 and an average degree of polymerization of about 1.5 were obtained. The infrared absorption spectrum of the resulting aluminum salt was as follows:

IR $\nu$ max cm$^{-1}$ : 3400 (—OH); 1757 (—OCOCH$_3$); 1600 (—COO$^-$).

EXAMPLE 17

3.8 g of triethyl aluminum were dissolved in 70 ml of tetrahydrofuran. Under ice cooling, a solution of 10.8 g of o-acetoxybenzoate dissolved in 200 ml of tetrahydrofuran was added dropwise little by little to the above solution in nitrogen gas current. After completion of the dropwise addition, the temperature of the mixture was returned to room temperature, and it was thrown into a great quantity of water. The precipitated crude crystals were recovered by filtration and dried under reduced pressure to yield 10 g of white aluminum tris-(o-acetoxybenzoate) having a molecular weight of about 545 and an average degree of polymerization of about 1. The infrared absorption spectrum of the resulting salt was as follows:

IR $\nu$ max cm$^{-1}$ : 1760 (—OCOCH$_3$); 1605 (—COO$^{-1}$).

EXAMPLE 18

3.73 g of di-isobutyl monoethoxy aluminum were dissolved in 150 ml of benzene, and the solution was maintained under ice cooling. A solution of 7.2 g of o-acetoxybenzoic acid dissolved in 100 ml tetrahydrofuran was added dropwise little by little to the above benzene solution under nitrogen gas current. After completion of the dropwise addition, the temperature of the mixture was returned at room temperature, and the reaction was carried out for 2 hours under agitation. Then, 10 ml of water were added to the reaction mixture and the reaction was continued further for another hour. After completion of the reaction, the solvent was distilled off under reduced pressure, and the residue was thrown into 200 ml of water. The precipitated powder was recovered by filtration. As a result 6.8 g of white monohydroxy aluminum bis-(o-acetoxybenzoate) having a molecular weight of about 560 and an average degree of polymerization of about 1.4 were obtained. The infrared absorption spectrum of the resulting aluminum salt was as follows:

IR $\nu$ max cm$^{-1}$ : 3400 (—OH) 1757 (—OCOCH$_3$); 1600 (—COO$^-$).

EXAMPLE 19

3.96 g of tri-isobutyl aluminum were dissolved in 100 ml of benzene, and the solution was maintained at 15° C. under nitrogen gas current by ice cooling. A solution of 8.28 g of salicylic acid dissolved in 100 ml of tetrahydrofuran was added dropwise little by little to the above benzene solution. After completion of the dropwise addition, the reaction was further carried out for 2 hours at room temperature under agitation. After completion of the reaction, the solvent was distilled off under reduced pressure to yield 7.5 g of aluminum tris-(o-hydroxybenzoate) in the form of a white powder having a melting point above 300° C. The resulting aluminum salt had a molecular weight of about 530, and the average degree of polymerization was found to be about 1.2. The infrared absorption spectrum of the salt is as follows:

IR $\nu$ max cm$^{-1}$ : 1605 (—COO$^-$).

EXAMPLE 20

120 mg of tri-isobutyl aluminum were dissolved in 50 ml of tetrahydrofuran, and the solution was maintained at 15° C. under nitrogen gas current by ice cooling. A solution of 640 mg of 1-(p-chlorobenzoyl)-2-methyl-5-methoxy-3-indolyl-acetic acid dissolved in 50 ml of tetrahydrofuran was added dropwise little by little to the above tetrahydrofuran solution. After completion of the dropwise addition, the temperature of the mixture was returned to room temperature, and the reaction was carried out for 1 hour under agitation. After completion of the reaction, the solvent was distilled off under reduced pressure to yield 610 mg of yellow powder of aluminum tris-[1-(4'-chlorobenzoyl)-2-methyl-5-methoxy-indolyl-3-acetate] which had a molecular weight of about 1200 and an average degree of polymerization of about 1.1. The infrared absorption spectrum of the resulting aluminum salt was as follows:

IR $\nu$ max cm$^{-1}$ : 1593 (—COO$^-$), 1680 (N—CO), 1480 1330, 1230, 1098, 762

EXAMPLE 21

70 mg of triethyl aluminum were dissolved in 50 ml of tetrahydrofuran, and the solution was maintained at −30° C. under nitrogen gas current. A solution of 640 mg of 1-(p-chlorobenzoyl)-2-methyl-5-methoxy-3-indolyl-acetic acid dissolved in 50 ml of tetrahydrofuran was added dropwise little by little to the above tetrahydrofuran solution. After completion of the dropwise addition, the temperature of the mixture was returned to room temperature. The solvent was distilled off under reduced pressure to yield 620 mg of yellow powder which was determined to be aluminum tris-[1-(4'-chlorobenzoyl)-2-methyl-5-methoxy-3-indolyl-acetate]. The molecular weight of the resulting aluminum salt was about 1020, and the average degree of polymerization was about 1.

EXAMPLE 22

4 g of tri-isobutyl aluminum were dissolved in 150 ml of benzene, and the solution was cooled to 15° C. with ice. While nitrogen gas was being introduced into the tri-isobutyl aluminum solution, a solution of 5.62 g of N-(3'-trifluoromethylphenyl)-anthranilic acid dissolved in 50 ml of benzene was added dropwise little by little to the above solution. After completion of the dropwise addition, the mixture was agitated for 10 minutes, and a solution of 7.2 g of o-acetoxybenzoic acid dissolved in 100 ml of benzene was added little by little to the mixture. After completion of the addition of the o-acetoxybenzoic acid solution, the mixture was agitated for 10 minutes. Distillation of the benzene under reduced pressure gave 12 g of powdery aluminum mono-[N-(3'-trifluoromethylphenyl)-anthranilate] bis-(o-acetoxybenzoate) which had a melting point of 135°– 142° C. The resulting aluminum salt had a molecular weight of about 800 and the average degree of polymerization waas found to be about 1.2. The infrared absorption spectrum of the salt was as follows:

IR $\nu_{max}^{KBr}$ cm$^{-1}$ : 3320, 1750, 1608, 1420

EXAMPLE 23

4 g of tri-isobutyl aluminum were dissolved in 150 ml of tetrahydrofuran, and the solution was cooled to 5° C.

with dry ice. Under nitrogen gas current a solution of 3.6 g of o-acetoxybenzoic acid dissolved in 50 ml of tetrahydrofuran was added dropwise little by little to the tri-isobutyl aluminum solution. After completion of the dropwise addition, the mixture was agitated for 10 minutes, and a solution of 11.24 g of N-(3'-trifluoromethylphenyl)-anthranilic acid dissolved in 100 ml of tetrahydrofuran was added little by little to the mixture, following which agitation was conducted for 10 minutes. After completion of the reaction, the tetrahydrofuran was distilled off. As a result, 13 g of powdery aluminum mono-(o-acetoxybenzoate) bis-[N-(3'-trifluoromethylphenyl)-anthranilate] having a melting point of 106°–115° C were obtained. The resulting aluminum salt had a molecular weight of about 840 and an average degree of polymerization of about 1.1 The infrared absorption spectrum of the salt was as follows:

IR $\nu_{max}^{KBr}$ cm$^{-1}$ : 3322, 1740, 1610, 1420

EXAMPLE 24

3.96 g of tri-isobutyl aluminum were dissolved in 150 ml of benzene, and the solution was maintained at 15° C. by ice cooling. Under nitrogen gas current a solution of 4.58 g of 4,5-dihydronaphth[2,1-d]isoxazolyl-3-acetic acid dissolved in 50 ml of tetrahydrofuran was added dropwise little by little to the above benzene solution. After completion of the dropwise addition, a solution of 11.2 g of N-(m-trifluoromethylphenyl)-anthranilic acid dissolved in 50 ml of tetrahydrofuran was added dropwise little by little to the reaction mixture. After completion of the dropwise addition, the temperature of the mixture was returned to room temperature, and the reaction was carried out for 2 hours under agitation. After completion of the reaction, distillation of the solvent under reduced pressure gave 12 g of aluminum mono-(4,5-dihydronaphth[2,1-d]isoxazolyl-3-acetate) bis-[N-(3'-trifluoromethylphenyl)-anthranilate] having a melting point above 123° C. The resulting aluminum salt had a molecular weight of 1000 and average degree of polymerization of 1.3. The infrared absorption spectrum of the salt was as follows:

IR $\nu$ max cm$^{-1}$ : 3320 (—NH); 1583 (—COO$^-$).

EXAMPLE 25

2.5 g of triethyl aluminum were dissolved in 100 ml of dimethoxyethane, and the solution was cooled to 25° C. under ice cooling. While nitrogen gas was being introduced into the solution, a solution of 5.62 g of N-(3'-trifluoromethylphenyl)-anthranilic acid dissolved in 50 ml of benzene was added dropwise little by little to the above methoxyethane solution. After completion of the dropwise addition, the mixture was agitated for 10 minutes, and a solution of 4.92 g of isonicotinic acid dissolved in 100 ml of benzene was added little by little to the mixture, followed by agitation. After completion of the reaction, the solvent was distilled to yield 10 g of powdery aluminum mono-[N-(3'-trifluoromethylphenyl)-anthranilate] bis-(pyridine-4-carboxylate) having a decomposition point above 300° C. The resulting aluminum salt had a molecular weight of about 750 and an average degree of polymerization of about 1.4. The infrared absorption spectrum of the salt was as follows:

IR $\nu_{max}^{KBr}$ cm$^{-1}$ : 3325, 1617, 1420.

EXAMPLE 26

1.23 g of triethyl aluminum was dissolved in 10 ml of dried dimethoxyethane in a reaction flask, and the temperature was lowered to −10° C. by cooling the outside of the flask with dry ice and 2-methoxyethanol. Under nitrogen gas current, a solution of 3.27 g of 4-amino-2-hydroxy-benzoic acid dissolved in 20 ml of dried dimethoxyethane was added dropwise to the above solution so that the liquid temperature did not exceed 10° C. After completion of the dropwise addition, 2 ml of water were added to the reaction mixture and agitation was carried out. Then, the reaction mixture was added to 500 ml of water, and the precipitated powder was recovered by filtration and dried to yield 3.10 g of aluminum bis-(4-amino-2-hydroxybenzoate) having a molecular weight of about 300 and an average degree of polymerization of about 1. The infrared absorption spectrum of the salt was as follows:

IR $\nu_{max}^{KBr}$ cm$^{-1}$ : 3542, 1580, 1452.

EXAMPLE 27

1.23 g of triethyl aluminum was dissolved in 10 ml of dried dimethoxyethane in a reaction flask, and the temperature was lowered to −10° C. by cooling the outside of the flask with dry ice and 2-ethoxyethanol. Under nitrogen gas current, a solution of 6.0 g of N-(3'-trifluoriomethylphenyl)-anthranilic acid dissolved in 10 ml of dried dimethoxyethane was added to the above solution in the flask. Then, a solution of 1.63 g of 4-amino-2-hydroxybenzoic acid dissolved in 10 ml of dimethoxyethane was added dropwise to the mixture. After completion of the dropwise addition, 2 ml of water were added to the reaction mixture and it was agitated. Then, the reaction mixture was added to 500 ml of water, and the precipitated powder was recovered by filtration and dried to yield 6.25 g of aluminum mono-(4-amino-2-hydroxybenzoate) bis-[N-(3'-trifluoromethylphenyl)-anthranilate] having a molecular weight of about 750 and an average degree of polymerization of about 1. The infrared absorption spectrum of the resulting salt was as follows:

IR $\nu_{max}^{KBr}$ cm$^{-1}$ : 3325, 1583, 1420

EXAMPLE 28

1.23 g of triethyl aluminum was dissolved in 10 ml of dried dimethoxy ethane in a reaction flask, and the temperature was lowered to −10° C. by cooling the outside of the flask with dry ice and 2-methoxyethanol. Under nitrogen gas current, a solution of 4.90 g of 4,5-dihydronaphth[2,1-d]isoxazolyl-3-acetic acid dissolved in 10 ml of dimethoxyethane was added to the cooled solution in the flask, and a solution of 1.63 g of 4-amino-2-hydroxybenzoic acid dissolved in 10 ml of dimethoxyethane was further added thereto dropwise. Just after completion of the dropwise addition, 2 ml of water were added to the reaction mixture, and it was agitated. Then, the reaction mixture was added to 500 ml of water, and the precipitated powder was recovered by filtration and dried to yield 4.86 g of aluminum mono-(4-amino-2-hydroxybenzoate) bis-[4,5-dihydronaphth[2,1-d]isoxazolyl]-3-acetate] having a molecular weight of about 620 and an average degree of polymerization of about 1. The infrared absorption spectrum of the resulting aluminum salt was as follows:

IR $\nu_{max}^{KBr}$ cm$^{-1}$ : 3321, 1593, 1430.

EXAMPLE 29

1.23 g of triethyl aluminum was dissolved in 10 ml of dried dimethoxyethane in a reaction flask, and the temperature was lowered by cooling the outside of the flask with dry ice and 2-methoxyethanol. Under nitrogen gas current, a solution of 6.0 g of N-(3'-trifluoromethylphenyl)-anthranic acid dissolved in 10 ml of dried dimethoxyethane was added dropwise to the above triethyl aluminum solution so that the temperature of the reaction mixture did not exceed 10° C. After completion of the drowpwise addition, 10 ml of water were added to the reaction mixture, and agitation was effected at room temperature for 30 minutes. The reaction mixture was then added to 500 ml of water, and the precipitated powder was recovered by filtration and dried to obtain 5.2 g of monohydroxy aluminum bis-[N-(3'-trifluoromethylphenyl)-antharanilate] having a molecular weight of about 800 and an average degree of polymerization of about 1.3. The infrared absorption spectrum of the resulting aluminum salt was as follows:

IR $\nu_{max}^{KBr}$ cm$^{-1}$ : 3330, 1582, 1418.

What we claim is:

1. A low polymer of aluminum tris-(o-acetoxybenzoate) obtained by polymerizing the monomer through coordination bonds.

2. A low polymer of monohydroxy aluminum bis-(o-acetoxybenzoate) obtained by polymerizing the monomer through coordination bonds.

3. A low polymer of aluminum tris-[N-(3'-trifluoromethylphenyl)-anthranilate] obtained by polymerizing the monomer through coordination bonds.

\* \* \* \* \*

UNITED STATES PATENT AND TRADEMARK OFFICE
CERTIFICATE OF CORRECTION

PATENT NO. : 3,988,333
DATED : October 26, 1976
INVENTOR(S) : SUZUKI, ET AL.

It is certified that error appears in the above-identified patent and that said Letters Patent are hereby corrected as shown below:

Please insert the following Foreign Application Priority Data:
-- Mar. 22, 1971 Japan...........46/16070
   Nov. 2, 1971 Japan...........46/86737
   Nov. 2, 1971 Japan...........46/86738
   Mar. 7, 1972 Japan...........47/22767 --

Signed and Sealed this

Thirteenth Day of March 1979

[SEAL]

Attest:

RUTH C. MASON
Attesting Officer

DONALD W. BANNER
Commissioner of Patents and Trademarks